United States Patent
Kensek

(10) Patent No.: US 6,676,955 B2
(45) Date of Patent: Jan. 13, 2004

(54) METHOD AND COMPOSITION FOR INSECT AND ANIMAL CONTROL

(75) Inventor: Lon Kensek, Andover, MN (US)

(73) Assignee: William L. Mateo, Cos Cob, CT (US)

( * ) Notice: Subject to any disclaimer, the term of this patent is extended or adjusted under 35 U.S.C. 154(b) by 22 days.

(21) Appl. No.: 09/832,624

(22) Filed: Apr. 11, 2001

(65) Prior Publication Data

US 2003/0091531 A1 May 15, 2003

(51) Int. Cl.7 .............................................. A01N 25/10
(52) U.S. Cl. ....................... 424/405; 424/406; 424/407; 514/675; 523/122
(58) Field of Search ................................ 424/405–407, 424/409, 78.02, 78.03, 78.07, DIG. 10; 514/675; 523/122

(56) References Cited

U.S. PATENT DOCUMENTS

| | | | | |
|---|---|---|---|---|
| 3,474,176 A | * | 10/1969 | Freeman | 424/331 |
| 3,853,532 A | * | 12/1974 | Rein et al. | 71/78 |
| 3,857,934 A | * | 12/1974 | Bernstein et al. | 424/30 |
| 4,855,127 A | * | 8/1989 | Abrutyn et al. | 424/411 |
| 5,792,467 A | * | 8/1998 | Emerson et al. | 424/405 |
| 6,395,290 B2 | * | 5/2002 | Brown | 424/408 |

* cited by examiner

*Primary Examiner*—Neil S. Levy
(74) *Attorney, Agent, or Firm*—Patrick J. Walsh

(57) ABSTRACT

Insect and animal control compositions and method in which a polymer and solvent are selected to provide a cross-linked film with matrices of sufficient capacity for trapping and being plated by an active ingredient particularly methyl nonyl ketone and other ingredients such as UV light absorber and fragrance, near transparency to UV light, flexibility, and susceptibility to slow degradation by environmental factors so to release the active ingredient, and the composition sprayed onto an area to be controlled.

2 Claims, No Drawings

METHOD AND COMPOSITION FOR INSECT AND ANIMAL CONTROL

BACKGROUND OF THE INVENTION

The present invention relates to insect and animal control compositions and insect repellent compositions effective against iris borers, other borers, and sucking or chewing insects, and animal repellent compositions especially effective against deer, elk, squirrels, chipmunks, rodents, rabbits and other warm-blooded mammals browsing on ornamental plants, trees and non-food crops. The invention also provides a method for insect and animal control utilizing the composition.

In one aspect, the invention is directed to insect control and the invention is described by way of illustrative application as a deterrent or control for iris borers for which there is presently no satisfactory means of control. Iris borers have a particularly destructive effect on irises and are highly detrimental to cost and labor invested in irises by growers and gardeners. Iris growers regard the iris borer as the biggest problem to be faced in growing irises in North America. The Cooperative Extension Institute of Agriculture and Natural Resources of the University of Nebraska states that the iris borer is the most serious insect pest of iris in Nebraska and is found virtually everywhere in the state.

The life cycle of iris borers includes four stages: egg, larva (borer or caterpillar), pupa, and finally the adult night-flying moth. The moths appear in September or October, lay eggs on and near iris plants which hatch in the spring as larvae. The larvae feed on new growth, bore into leaf sheaths and eat their way into the base and rhizome. In late summer the larvae leave hollowed out rhizomes and pupate in the nearby soil. The moths emerge in about a month beginning a new cycle of life and iris destruction.

There are four principal methods for controlling the iris borer: the practice of garden hygiene especially in the spring and autumn, use of pesticides, particularly Cygon 2E, introduction of beneficial nematodes into the soil, and physical search and destroy methods.

Garden hygiene practice involves spring and fall garden clean-up, physical removal of any larvae found, squeezing of leafs where there is evidence of boring or mining in leaf sheaths. If larvae have tunnelled from the base into the rhizome, the plants must be dug up, the rhizomes examined, and any borers or rot caused by them removed by cutting away. The rhizome is then left in the sun to dry and scab over for several days. Before replanting in the soil, the planted area must be sifted by hand to remove any borers or pupae. Following this treatment, the transplanted rhizomes may not bloom for one or two years. This practice is neither a satisfactory nor complete means of control.

Iris growers use Cygon 2E (dimethoate) pesticide as the standard recommended chemical for killing borers and their larvae. Dimethoate is a powerful chemical and only is effective for ten days to two weeks in the spring. After that point the borers are beneath the ground and so large that no reasonable chemical control is effective. Chemicals will have no effect on borers that have penetrated iris rhizomes.

Dimethoate is highly toxic and kills beneficial as well as undesirable organisms. It is classified by the EPA as a group 3 carcinogen. By agreement of the EPA and the manufacturer, dimethoate will not be re-registered by the EPA pesticide review program for residential use.

Nematodes are used to find and destroy borers, however, nematodes themselves must be controlled since high populations retard healthy plant growth. Nematode controls are chemical as well as biological and are considered unsatisfactory in presenting a new set of problems including chemical contamination and expense.

In another aspect, the invention is directed to animal control particularly control of deer, elk, squirrels, chipmunks, rodents, rabbits and other warm-blooded mammals. In recent years animal population has grown to a point as to be present in significant numbers. These animals are considered pests when they feed on ornamental and other plants, trees, bulbs, seed and rhizomes and non-food crops cultivated with considerable investment in plants, equipment and labor.

The present invention utilizes methyl nonyl ketone as active ingredient in achieving insect and animal control. Methyl nonyl ketone (known also as undecanone-2) is a well-known insect repellent, insecticide, and animal repellent being disclosed in prior United States patents, and registerable for use as a pesticide by the United States Environmental Protection Agency. U.S. Pat. No. 4,555,015 to Haase discloses methyl nonyl ketone applied to plastic film bags as an animal repellent. U.S. Pat. No. 4,775,532 to Clayton discloses methyl nonyl ketone carried by dialkhyl adipate for use as an animal repellent. U.S. Pat. No. 3,474,176 to Freeman discloses methyl nonyl ketone admixed with isopropanol, and also admixed with petroleum distillate and polyethelene glycol emulsifier with each mixture used as an animal repellent spray from a pressurized aerosol dispensing container. U.S. Pat. No. 2,283,471 to Swaine discloses methyl nonyl ketone with benzene triethanolamine-oleate and water for use as an insecticide. U.S. Pat. No. 4,169,898 to Haase discloses methyl nonyl ketone mixed with 3-phenylpropenal for use as an animal repellent, particularly dogs and cats. U.S. Pat. No. 4,562,794 to Speckman discloses methyl nonyl ketone among other active ingredients dispensed by a device worn by an animal for dealing with ectoparasites. U.S. Pat. No. 4,338,352 to Allan discloses methyl nonyl ketone released from biodegradable, microporous structures such as never-dried wood pulp for use as a repellent. U.S. Pat. No. 6,001,874 to Veierov discloses a number of conventional "behavior interfering compounds" including methyl nonyl ketone applied by means of an agricultural oil.

Methyl nonyl ketone is highly effective as an insect and animal repellent, however, methyl nonyl ketone has a twelve hour shelf life and degrades rapidly under exposure to ultraviolet light, water and oxygen, and by exposure to microbes in the soil. The present invention is directed to a composition for stabilizing methyl nonyl ketone to substantially improve its usefulness as an insect and animal repellent and, by way of illustrative application, its usefulness in repelling iris borers. The invention also provides a method for insect and animal control in using the composition.

SUMMARY OF THE INVENTION

The compositions of this invention comprise an active ingredient dispersed in an alcohol/polymer solution wherein when the alcohol evaporates to leave a polymer film, the polymer cross-links binding the active ingredient within the polymer film matrices. Polymers and combinations of polymers are chosen so as to determine both the amount of active and other ingredients trapped within the polymer film matrices, the rate of degradation of the polymer matrix which affects the rate of release of the active ingredient under various environmental conditions, as well as the flexibility of the polymer film. Fragrance ingredients are selected to modify product smell and taste, and in some cases fragrance ingredients may act as film modifiers to enhance or retard film flexibility. An ultraviolet light absorber is bound into the polymer matrices to extend the lifetime of the active ingredient under ultraviolet light conditions. Compositions according to the invention may also include pH adjusters.

Compositions according to the invention are suitable for applying using conventional containers with manual dispensing pumps, aerial application, or by means of power assisted spray mechanisms.

In the method according to the invention, an active ingredient is mixed with solvent and environmentally soluble polymer or copolymer and with other ingredients to form a composition, the composition is sprayed on the area for insect and animal control, the solvent evaporates, the polymer or copolymer cross-links to form a flexible film having interstices, active and other ingredients are trapped in the polymer film interstices, the polymer or copolymer film degrades under environmental influences, and the active ingredient and other ingredients are released to control insects of animals.

A pesticide according to the invention containing methyl nonyl ketone as active ingredient is registered by the United States EPA and is the only pesticide containing methyl nonyl ketone so registered.

Specific examples are included in the following description for purposes of clarity, but various details can be changed within the scope of the present invention.

OBJECTS OF THE INVENTION

An object of the invention is to provide an insect repellent composition that is particularly effective in deterring insects including the iris borer in moth to pupae stages.

Another object of the invention is to provide a method for controlling insects and animals.

An object of the invention is to provide an animal control composition that is particularly effective in deterring animals including deer, elk, squirrels, chipmunks, rodents, rabbits and other warm-blooded mammals from browsing on shrubbery, and on ornamental plants and their germinated and ungerminated rhizomes, roots, bulbs, seeds, and tubers.

An object of the invention is to provide an animal control composition that is particularly effective in deterring canines and felines from areas to which the composition is applied.

Another object of the invention is to provide an insect and animal control composition having methyl nonyl ketone as an active ingredient.

Another object of the invention is to provide an insect and animal control composition for stabilizing and extending the useful lifetime of methyl nonyl ketone as the active ingredient.

Another object of the invention is to provide an insect and animal control composition containing other ingredients including fragrances, UV light absorbers, and pH adjusters to enhance to useful life of the composition.

Another object of the invention is to provide an insect and animal control composition of high efficacy and safety for applying from household containers, commercial spraying equipment, aerial application, and other home and agricultural application.

Another object of the invention is to provide an insect and animal control composition that is particularly effective in deterring rodents particularly squirrels, chipmunks, and rabbits from consuming food in bird feeding stations.

Other and further objects of the invention will become apparent with an understanding of the following detailed description of the invention or upon employment of the invention in practice.

A preferred embodiment of the invention has been chosen for detailed description to enable those having ordinary skill in the art to which the invention appertains to readily understand how to make and use the invention.

DETAILED DESCRIPTION OF THE PREFERRED EMBODIMENT

The preferred insect and animal repellent composition according to a preferred embodiment of the invention comprises solvent, polymer, active ingredient, fragrance ingredient, water, UV light absorber, and pH adjuster.

The active ingredient is methyl nonyl ketone which has a useful life primarily limited by exposure to ultraviolet light and soil microbes, is chemically relatively stable although it can be oxidized, and is somewhat volatile.

A polymer or mixture of polymers is selected according to the invention for cross-linking or curing to form interstices or a matrix within a three dimensional structure film which trap and protect methyl nonyl ketone from oxidation. The relative sizes of the interstices can be somewhat modified by selection of polymer or combination of polymers. Another aspect of polymer or polymer combination selection is to achieve film flexibility without brittleness and without excessive flexibility. A brittle film ruptures and flakes off when the ambient temperature drops, whereas an excessively flexible film has some of the characteristics of a liquid and binds the methyl nonyl ketone poorly.

The polymer film also acts as a physical barrier to soil microbes to some degree. Soil microbes will slowly degrade the polymeric film, and as the film degrades, the trapped methyl nonyl ketone is released. Environmental factors such as water, oxygen and ultraviolet light also degrade the polymer film again slowly releasing methyl nonyl ketone into the specific environment. The fragrance ingredient is also trapped in the film interstices for release as the film degrades.

Some methyl nonyl ketone plates the outer surfaces of the polymer film and is available for immediate dispersal into the environment, and subsequently for immediate environmental degrading. The fragrance also plates and is released immediately to the environment.

Polymers selected are nearly transparent to ultraviolet light, however, UV light absorbers are also captured within the film matrices and plate the polymeric film. By selecting UV light absorber's and percentages thereof, the speed of polymer film degradation is controlled.

In sum, a polymeric film is selected to provide a cross-linked film with matrices of sufficient capacity for trapping and being plated by active and other ingredients such as UV light absorber and fragrance, to have near transparency to UV light, flexibility without brittleness or being too flexible, and to have solubility of the cured polymer, that is, susceptibility to slow degradation by environmental factors including water, oxygen, UV light, and soil microbes.

Suitable polymers include polyvinylpyrrolidinone homo polymer, polyvinylpyrrolidinone/vinyl acetate copolymer, polyvinyl methyl ether/maleic anhydride copolymer, butyl ester of polyvinyl methyl ether/maleic anhydride copolymer, ethyl ester of polyvinyl methyl ether/maleic anhydride copolymer, isopropyl ester of polyvinyl methyl ether/maleic anhydride copolymer brassica campestris/aleurites fordi oil copolymer, acrylamide copolymer, acrylamide/sodium acrylate copolymer, acrylates copolymer, acrylates/acrylamide copolymer, acrylates/dimethicone copolymer, octylacrylamide/acrylates/butylaminoethyl meth-acrylate copolymer or various mixtures of the above.

Suitable solvents include ethanol, methanol, and isopropanol. Ethanol is preferred because of its lower toxicity. The preferred or alternate solvents are used within the same percentage ranges given below.

Fragrance ingredients include castor oil, eugenol, black pepper oil, acetyl triethyl citrate, actyl tributyl citrate, triethyl citrate, camphor, diethylhexyl phthlate, or various mixtures of the above.

Ultraviolet light absorbers include benzophenone-3, ethylhexyl methoxycinnamate, or similar absorbers.

Suitable pH adjusters include hydrochloric acid, phosphoric acid, sodium hydroxide, and aminomethylpropanol (referred to as AMP).

The active ingredient is methyl nonyl ketone.

Suitable formulas in percent by volume comprise compositions of ingredients within the following ranges:

solvent in a range of 30–90%, and preferably 46.15%;

polymer in a range of 0.5–8%, and preferably between 1.75–2.25%;

active ingredient in a range of 0.5–10%, and preferably between 1.75–2.25%;

fragrance ingredient in a range of 0.01–25%, and preferably between 0.1–0.4%;

ultra violet light absorbers in a range of 0.0001–9.0%;

water in a range of 0.01–50%, and preferably between 48.95–50.25%, and;

pH adjusters in a range of 0.0001–5%, and preferably 0.9512%.

The composition is prepared by measuring solvent into a mixing tank, adding polymer, active ingredient, fragrance ingredient, and water in that order then mixing until uniform.

Specific examples of the preferred compositions are:

EXAMPLE 1

| Polymers: | 3.6051% | octylacrylamide/acrylates/butylaminoethyl methacrylate copolymer, |
| --- | --- | --- |
| | 6.1102% | acrylates copolymer, |
| pH adjuster: | 0.9512% | AMP |
| Active ingredient: | 2.2451% | methyl nonyl ketone, |
| Sunscreen: | 2.1614% | benzophenone-3 |
| Fragrance ingredient: | 0.4431% | acetyl tributyl citrate, |
| Water: | 28.3628%, | |
| Solvent: | 56.0107% | ethyl alcohol. |

The formula is prepared as stated above.

This example 1 composition provides an insect repellent to treat bulbs and/or rhizomes to reduce insect damage to germinating bulbs and rhizomes and to treat ornamental plants to reduce or eliminate insect damage to these plants. The composition also provides a repellent for animals including deer, elk, squirrels, chipmunks, rodents, rabbits and other warm-blooded mammals from browsing on shrubbery, and on ornamental plants and their germinated and ungerminated rhizomes, roots, bulbs, seeds, and tubers.

EXAMPLE 2

| Polymer: | 5.5170% | polyvinyl methyl ether/maleic anhydride copolymer |
| --- | --- | --- |
| Active ingredient: | 2.0600% | methyl nonyl ketone, |
| Sunscreen: | 3.1410% | benzophenone-3 |
| Fragrance: | 1.0490% | camphor, |
| Solvent: | 88.2330% | ethyl alcohol. |

The formula is prepared as stated above.

This example 2 composition provides a rodent repellent that may be used to treat birdseed to specifically repel squirrels.

EXAMPLE 3

| Polymer: | 4.5000% | ethyl ester of polyvinyl methyl ether/maleic anhydride copolymer |
| --- | --- | --- |
| Active ingredient: | 2.1236% | methyl nonyl ketone, |
| Fragrance ingredients: | 0.4431% | black pepper oil |
| | 13.3326% | castor oil |
| Solvent: | 79.6007% | ethyl alcohol (denatured SDA 40B). |

The formula is prepared as stated above.

This example 3 composition provides a rodent repellent that may be used to treat bulbs and/or rhizomes to repel rodents (specifically squirrels and chipmunks) so as to stop these animals from digging up dormant or germinating bulbs and/or rhizomes.

A composition prepared according to the invention is liquid and is applied using containers with a manual pump or automated. When sprayed onto plants, rhizomes, bulbs, seed and surrounding soil or onto ornamental plants the solvent in the composition evaporates and a flexible polymer film forms and cures with active, fragrance and ultraviolet light absorber ingredients trapped in matrices of the polymer film and plated on the film. The plated constituents including methyl nonyl ketone are available for immediate dispersal into the environment for deterring iris borers from the irises, or insects from non-food crops and ornamental plants, or deer, elk, squirrels, chipmunks, rodents, rabbits and other warm-blooded mammals from plants and the like, or canines and felines in areas controlled for their presence. The trapped constituents are gradually released from the polymer matrices as the film degrades under the influence of water, oxygen, ultraviolet light and soil microbes.

The method for controlling insects and animals according to the invention comprises the steps of selecting a polymer or copolymer for cross-linking to form a flexible, degradable film with interstices for trapping an active ingredient and a fragrance ingredient, mixing the polymer with a solvent, active ingredient and fragrance ingredient, applying the mixture on an area to be controlled for insects and animals so as to evaporate the solvent, to cross-link the polymer, to trap the active ingredients in cross-linked polymer interstices, and to degrade the film gradually under environmental influences, and gradually to release the active and fragrance ingredients to control insects and animals. The mixture can be applied by spraying, coating or any convenient technique for administering the composition to an area to be controlled for insects and animals.

Various changes may be made to the method and composition embodying the principles of the invention. The foregoing embodiments are set forth in an illustrative and not in a limiting sense. The scope of the invention is defined by the claims appended hereto. In the appended claims the term polymer has reference to polymers, copolymers, and mixtures of polymers and copolymers.

I claim:

1. A composition for controlling insects and animals comprising a mixture in percent by volume of:

(i) 0.5% to 8% of polymer selected from the group consisting of polyvinylpyrrolidinone, polyvinylpyrrolidinone/vinyl acetate, polyvinyl methyl ether/maleic anhydride, butyl ester of polyvinyl methyl ether/maleic anhydride, ethyl ester of polyvinyl methyl ether/maleic anhydride, isopropyl ester of polyvinyl methyl ether/maleic anhydride, brassica campestris/ aleurites fordi oil, acrylamide, acrylamide/sodium acrylate, acrylates, acrylates/acrylamide, acrylates/ dimethicone, octyl-acrylamide/acrylates/ butylaminoethyl methacrylate;

(ii) 30% to 90% of a solvent selected from the group consisting of ethanol, methanol, and isopropanol;

(iii) 0.1% to 25% of fragrance selected from the group consisting of castor oil, eugenol, black pepper oil, acetyl triethyl citrate, acteyl tributyl citrate, triethyl citrate, camphor, diethylhexyl phthlate;

(iv) 0.0001% to 9% of ultraviolet light absorber selected from the group consisting of benzophenone-3, ethylhexyl methoxycinnamate, (v) 0.0001% to 5.0% of pH adjuster selected from the group consisting of hydrochloric acid, phosphoric acid, sodium hydroxide, and aminomethylpropanol, and (vi) 0.5% to 15.0% of active ingredient methyl nonyl ketone.

2. A composition for controlling insects and animals comprising a mixture in percent by volume of:

| | |
|---|---|
| 3.6051% | octylacrylamide/acrylates/ butylaminoethyl methacrylate copolymer, |
| 6.1102% | acrylates copolymer, |
| 0.09512% | aminomethylpropanol |
| 2.2451% | methyl nonyl ketone, |
| 0.4431% | acetyl tributyl citrate, |
| 28.3628% | water, and |
| 56.0107% | ethyl alcohol. |

* * * * *